United States Patent [19]

Yamamoto et al.

[11] Patent Number: 5,126,307
[45] Date of Patent: Jun. 30, 1992

[54] PROCESS FOR PREPARING CATALYST FOR PRODUCING METHACRYLIC ACID AND CATALYST PREPARED BY PROCESS

[75] Inventors: Shinji Yamamoto; Motomu Oh-Kita, both of Otake, Japan

[73] Assignee: Mitsubishi Rayon Co., Ltd., Tokyo, Japan

[21] Appl. No.: 688,403

[22] Filed: Apr. 22, 1991

[30] Foreign Application Priority Data

Apr. 23, 1990 [JP] Japan ................... 2-105338

[51] Int. Cl.$^5$ .................. B01J 37/04; B01J 23/88; B01J 27/18; B01J 23/78
[52] U.S. Cl. .................. 502/200; 502/205; 502/209
[58] Field of Search .......... 502/209, 205, 200; 562/534, 535

[56] References Cited

U.S. PATENT DOCUMENTS

| | | | |
|---|---|---|---|
| 3,998,876 | 12/1976 | Kato et al. ................ | 502/200 X |
| 4,001,316 | 1/1977 | Ishimi ....................... | 502/209 X |
| 4,273,676 | 6/1981 | Matsumoto et al. ....... | 502/209 |
| 4,419,270 | 12/1983 | Ueshima et al. .......... | 502/209 |
| 4,467,113 | 8/1984 | Matsumoto et al. ....... | 502/209 X |
| 4,530,916 | 7/1985 | Matsumoto et al. ....... | 502/209 |
| 4,745,217 | 5/1988 | Matsumoto et al. ....... | 502/209 X |

FOREIGN PATENT DOCUMENTS

| | | | |
|---|---|---|---|
| 0350862 | 1/1989 | European Pat. Off. ..... | 562/535 |
| 2-022243 | 1/1990 | Japan . | |

OTHER PUBLICATIONS

Kirk-Othmer, *Encyclopedia of Chemical Technology*, 3rd ed., John Wiley & Sons, New York, 1978, vol. 2, pp. 471 and 516-536.

Kirk-Othmer, *Concise Encyclopedia of Chemical Technology*, John Wiley & Sons, 1985, New York, p. 92.

*Primary Examiner*—W. J. Shine
*Assistant Examiner*—Douglas J. McGinty
*Attorney, Agent, or Firm*—Armstrong, Nikaido, Marmelstein, Kubovcik & Murray

[57] ABSTRACT

A process for preparing a multi-component catalyst for producing methacrylic acid, containing phosphorus, molybdenum and vanadium, comprising mixing oxides of molybdenum and vanadium, water and materials for the other catalyst-constituting elements except potassium, rubidium, cesium and thallium to prepare a mixed solution, heating and reacting the mixed solution at 85° C. or more for 1 to 10 hours, then cooling the mixed solution to 80° C. or less, adding thereto a material for at least one element component selected from the group consisting of potassium, rubidium, cesium and thallium, adding further thereto at least one compound selected from the group consisting of ammonium nitrate, ammonium carbonate, ammonium hydrogencarbonate, ammonium sulfate and ammonium hydrogensulfate with the temperature of the mixed solution kept at 80° C. or less, then removing water therefrom and heat-treating the residual product. According to the present invention, a catalyst which works effectively at a lower reaction temperature and yet gives methacrylic acid in higher yields than when catalysts prepared by the conventional methods are used is prepared.

6 Claims, No Drawings

PROCESS FOR PREPARING CATALYST FOR PRODUCING METHACRYLIC ACID AND CATALYST PREPARED BY PROCESS

BACKGROUND OF THE INVENTION

1. Field of the Invention

The present invention relates to a process for preparing a catalyst used in producing methacrylic acid by the gas-phase catalytic oxidation of methacrolein.

2. Description of the Prior Art

Hitherto, in producing methacrylic acid by the gas-phase catalytic oxidation of methacrolein, it has been found to be advantageous to keep the yield high by operating at a low reaction temperature from the perspective of the life of the catalysts, inhibition of side reactions, cost of equipments, etc. However, when catalysts prepared by the conventional methods are used, satisfactory results are not always obtained.

One possible reason for this is that the specific surface area dimension and the distribution of micropores of the catalyst, which are important to the oxidation reaction, have not sufficiently been controlled. In order to improve these defects, the following various trials have been made at the time of preparation of the catalyst: Addition of a carboxylic acid or polyhydric alcohol (refer to Japanese Patent Application Kokai No. 51-136615), addition of an alcohol or glycol (refer to ibid, No. 55-73347), addition of pyridine or its derivative (refer to ibid. No. 47-38591, No. 57-171444), addition of quinoline or its derivative (refer to ibid. No. 60-209258), addition of aqueous ammonia or ammonium nitrate (refer to ibid. No. 57-165040), etc. However, these methods have various defects such that, for example, the reaction results are not satisfactory; the catalytic activity is largely reduced with the lapse of time; the reaction temperature is too high; and the heat-treatment method, which is a catalyst-activating treatment, is troublesome because of the use of organic substances. The catalysts thus obtained, therefore, are not satisfactory as industrial catalysts.

SUMMARY OF THE INVENTION

An object of the present invention is to provide a novel process for preparing a catalyst for advantageously producing methacrylic acid from methacrolein.

In order to improve the conventional catalyst-preparation methods, the present inventors have studied with particular notice given to the physical properties of the catalyst, and as a result have found a novel process for preparing a catalyst which works effectively at a lower reaction temperature and yet gives methacrylic acid in higher yields than when catalysts prepared by the conventional methods are used.

The present invention relates to a process for preparing a multi-component catalyst for producing methacrylic acid, containing phosphorus, molybdenum and vanadium, comprising mixing oxides of molybdenum and vanadium, water and materials for the other catalyst-constituting elements except, potassium, rubidium, cesium and thallium, to prepare a mixed solution, heating and reacting the mixed solution at 85° C. or more for 1 to 10 hours, then cooling the mixed solution to 80° C. or less, adding thereto a material comprising at least one element component selected from the group consisting of potassium, rubidium, cesium and thallium, adding further thereto at least one compound selected from the group consisting of ammonium nitrate, ammonium carbonate, ammonium hydrogen-carbonate, ammonium sulfate and ammonium hydrogensulfate maintaining the temperature of the mixed solution at 80° C. or less, then removing water therefrom; and heat-treating the residual product.

PREFERRED EMBODIMENTS OF THE INVENTION

The catalyst for producing methacrylic acid obtained according to the present invention preferably has a composition represented by the general formula:

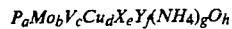

$$P_a Mo_b V_c Cu_d X_e Y_f (NH_4)_g O_h$$

wherein P, Mo, V, Cu, NH$_4$ and O are phosphorus, molybdenum, vanadium, copper, ammonium group and oxygen, respectively, X is at least one element selected from the group consisting of potassium, rubidium, cesium and thallium, Y is at least one element selected from the group consisting of silver, magnesium, zinc, arsenic, germanium, silicon, tungsten, boron, bismuth, chromium, lanthanum, barium, antimony, iron, zirconium, tellurium and cerium, and a, b, c, d, e, f and h are the atomic ratio of each element, and when b is 12, a is 0.5 to 3, c is 0.01 to 3, d is 0.01 to 2, e is 0.01 to 2 and f is 0 to 5, h is the number of oxygen atoms necessary to satisfy the valence of each component, and g is the number of ammonium groups being 0.01 to 2.

Materials for molybdenum and vanadium components used to prepare the catalyst include molybdenum trioxide, molybdic acid and other oxides. Particularly, good results are obtained when molybdenum trioxide and vanadium pentoxide are used.

As materials for other catalyst-constituting elements, the oxides, carbonates, acetates, hydroxides, etc. of the elements can be used in combination.

In practicing the present invention, first, materials for catalyst-constituting elements (comprising at least materials for molybdenum, vanadium and phosphorus), except materials for potassium, rubidium, cesium and/or thallium, are dissolved or dispersed in water.

As materials for the foregoing catalyst-constituting elements, in addition to the oxides of molybdenum and vanadium and phosphorus compounds, there are used for example the oxides, carbonates, acetates, hydroxides, etc. of copper, silver, magnesium, zinc, arsenic, germanium, silicon, tungsten, boron, bismuth, chromium, lanthanum, barium, antimony, iron, zirconium, tellurium and cerium.

Next, the aqueous solution or dispersion of the materials for catalyst is heated for 1 to 10 hours at 85° C. or more, preferably 90° C. or more. When the heating temperature is less than 85° C. or the heating time is less than 1 hour, it is difficult for the resulting catalyst to take on a heteropoly-acid structure effective for catalyzing the reaction. If the heating time is longer than the above value, a particular improvement in the effect is not observed.

After heating, the mixed solution containing the materials for catalyst is cooled to 80° C. or less, preferably 35° C. to 70° C., and materials comprising the potassium, rubidium, cesium and/or thallium components are added.

Next, at the temperature of the mixed solution of 80° C. or less, preferably 40° C. to 70° C., ammonium nitrate, ammonium carbonate, ammonium hydrogen carbonate, ammonium sulfate and/or ammonium hydrogensulfate are added. When the materials for potassium, rubidium, cesium and/or thallium components and the above ammonium compounds are added at a liquid temperature exceeding 80° C., it is difficult to prepare a catalyst for producing methacrylic acid in high yields.

The amount of ammonium nitrate, ammonium carbonate, ammonium hydrogen carbonate, ammonium sulfate and/or ammonium hydrogensulfate is 0.5 to 30 wt. %, particularly preferably 1 to 20 wt. % based on the total weight of the materials for the catalyst. When the amount of the ammonium compound is less than the above value, the performance of the catalyst is insufficient, and if it is more than the above value, a particular improvement in the effect is not observed.

Next, on heat-treating the mixture thus obtained, the desired catalyst is obtained.

It is desirable to carry out the heat-treatment, for example, at a temperature of 300° C. to 430° C. while streaming air and/or a gas containing 5 vol. % or more of oxygen. When the mixture is an aqueous solution or dispersion, it is usually desirable to carry out the heat-treatment after removal of water.

The catalyst obtained according to the present invention works effectively without a carrier, but it is preferred to use the catalyst supported on or diluted with an inert carrier such as silica, alumina, silica-alumina, silicon carbide, diatomaceous earth, etc.

When methacrylic acid is produced with the catalyst obtained by the present invention, a methacrolein-containing gas, a material, is used as the reactant. The methacrolein concentration in the gas can be varied in a wide range, but 1 to 20% by volume, particularly 3 to 10% by volume is preferred.

Methacrolein, a material, may contain small amounts of impurities such as water, a lower saturated aldehyde, etc. These impurities have substantially no effect on the reaction.

As an oxygen source, the use of air is economical, but air made rich in pure oxygen may be used if necessary. The oxygen concentration of the gas, a material, is determined by the molar ratio to methacrolein. The value of this molar ratio is 0.3 to 4, particularly preferably 0.4 to 2.5. The gas, a material, may be diluted with an inert gas such as nitrogen, steam, carbon dioxide, etc.

Reaction pressure is preferably normal pressure to several atmospheres.

Reaction temperature is 200° C. to 420° C., particularly preferably 230° C. to 400° C.

The reaction can be carried out by using either a fixed bed or fluidized bed.

In the following examples and comparative examples, the conversion of methacrolein and selectivity of methacrylic acid produced are defined as follows:

$$\text{Conversion of methacrolein (\%)} = \frac{\text{Number of moles of reacted methacrolein}}{\text{Number of moles of supplied methacrolein}} \times 100$$

$$\text{Selectivity of methacrylic acid (\%)} = \frac{\text{Number of moles of produced methacrylic acid}}{\text{Number of moles of reacted methacrolein}} \times 100$$

In the following examples and comparative examples, parts are by weight, and analyses were carried out by gas chromatography.

EXAMPLE 1

100 Parts of molybdenum trioxide, 2.6 parts of vanadium pentoxide and 6.7 parts of 85% phosphoric acid were added to 800 parts of pure water, and the resulting mixture was heated under reflux at 100° C. for 6 hours. Thereafter, 1.2 parts of copper acetate was added, and refluxing was continued at 100° C. for further 3 hours with heating. After refluxing, the mixed solution was cooled to 40° C., and 11.2 parts of cesium hydrogen carbonate dissolved in 100 parts of pure water was added, after which 5.6 parts of ammonium carbonate dissolved in 100 parts of pure water was further added with the temperature of the mixed solution kept at 40° C. The resulting mixed solution was evaporated to dryness with heating. The solid product obtained was dried at 120° C. for 16 hours, shaped by applying pressure and heat-treated at 380° C. for 5 hours under air stream. The composition of components except oxygen of the resulting catalyst was $P_1Mo_{12}V_{0.5}Cu_{0.1}Cs_1(NH_4)_{0.3}$ (catalysts described later also are represented by the composition of components except oxygen).

A reactor was charged with this catalyst, and a mixed gas consisting of 5 vol. % of methacrolein, 10 vol. % of oxygen, 30 vol. % of steam and 55 vol. % of nitrogen was passed through the reactor at a reaction temperature of 285° C. for a contact time of 3.6 seconds. The products were collected and analyzed by gas chromatography to find that the conversion of methacrolein was 85.8% and the selectivity of methacrylic acid was 83.9%.

COMPARATIVE EXAMPLE 1

A catalyst was prepared in the same manner as in Example 1 except that, after the refluxing, cesium hydrogen carbonate was added with the temperature of the mixed solution kept at 100° C., and then ammonium carbonate also with the temperature of the mixed solution kept at 100° C. Using this catalyst, reaction was carried out under the same conditions as in Example 1 to find that the conversion of methacrolein was 84.1% and the selectivity of methacrylic acid was 83.8%.

COMPARATIVE EXAMPLE 2

A catalyst was prepared in the same manner as in Example 1 except that, after the refluxing, the mixed solution was cooled to 40° C. and then ammonium carbonate was added, after which cesium hydrogen carbonate was further added with the temperature of the mixed solution kept at 40° C. Using this catalyst, reaction was carried out under the same conditions as in Example 1 to find that the conversion of methacrolein was 84.8% and the selectivity of methacrylic acid was 84.0%.

COMPARATIVE EXAMPLE 3

A catalyst was prepared in the same manner as in Example 1 except not adding ammonium carbonate. Using this catalyst, reaction was carried out under the same conditions as in Example 1 except that the reaction temperature was changed to 290° C. As a result, it was found that the conversion of methacrolein was 80.6% and the selectivity of methacrylic acid was 81.6%.

EXAMPLE 2

A catalyst having a composition, $P_1Mo_{12}V_{0.5}Cu_{0.1}K_1Si_{0.3}As_{0.2}(NH_4)_{0.2}$, was prepared according to Example 1 except that 9.2 parts of ammonium hydrogen carbonate per 100 parts of molybdenum trioxide was added in place of ammonium carbonate. Using this catalyst, reaction was carried out under the same conditions as in Example 1 except that the reaction temperature was changed to 270° C. As a result, it was found that the conversion of methacrolein was 86.2% and the selectivity of methacrylic acid was 86.8%.

COMPARATIVE EXAMPLE 4

A catalyst was prepared in the same manner as in Example 2 except that, after the refluxing, potassium carbonate was added with the temperature of the mixed solution kept at 100° C., and then ammonium hydrogen carbonate was added with the temperature of the mixed solution kept at 100° C. Using this catalyst, reaction was carried out under the same conditions as in Example 1 to find that the conversion of methacrolein was 84.3% and the selectively of methacrylic acid was 86.6%.

COMPARATIVE EXAMPLE 5

A catalyst was prepared as in the same manner as in Example 2 except that, after the refluxing, the mixed solution was cooled to 40° C. and ammonium hydrogen carbonate was added, after which potassium carbonate was further added with the temperature of the mixed solution kept at 40° C. Using this catalyst, reaction was carried out under the same conditions as in Example 1 except that the reaction temperature was changed to 270° C. As a result, it was found that the conversion of methacrolein was 85.1%. and the selectivity of methacrylic acid was 86.7%.

COMPARATIVE EXAMPLE 6

A catalyst was prepared in the same manner as in Example 2 except not adding ammonium hydrogen carbonate. Using this catalyst, reaction was carried out under the same conditions as in Example 1 except that the reaction temperature was changed to 280° C. As a result, it was found that the conversion of methacrolein was 79.3% and the selectivity of methacrylic acid was 84.2%.

EXAMPLE 3

A catalyst having a composition, $P_{1.5}Mo_{12}V_{0.8}Cu_{0.2}Rb_1Ce_{0.1}Fe_{0.2}Sb_{0.8}(NH_4)_{0.4}$, was prepared according to Example 1 except that a part of ammonium carbonate was replaced by ammonium hydrogen carbonate and a mixed solution containing 2.8 parts of ammonium carbonate and 4.6 parts of ammonium hydrogen carbonate per 100 parts of molybdenum trioxide was added. In this case, antimony trioxide was used as a source of antimony.

Using this catalyst, reaction was carried out under the same conditions as in Example 1 except that the reaction temperature was changed to 270° C. As a result, it was found that the conversion of methacrolein was 91.3% and the selectivity of methacrylic acid was 88.9%.

COMPARATIVE EXAMPLE 7

A catalyst was prepared in the same manner as in Example 3 except that, after the refluxing, rubidium acetate was added with the temperature of the mixed solution kept at 100° C., and then a mixed solution of ammonium carbonate and ammonium hydrogen carbonate was added with the temperature of the mixed solution kept at 100° C. Using this catalyst, reaction was carried out under the same conditions as in Example 1 except that the reaction temperature was changed to 270° C. As a result, it was found that the conversion of methacrolein was 89.7% and the selectivity of methacrylic acid was 88.8%.

COMPARATIVE EXAMPLE 8

A catalyst was prepared in the same manner as in Example 3 except not adding ammonium carbonate nor ammonium hydrogen carbonate. Using this catalyst, reaction was carried out under the same conditions as in Example 1 except that the reaction temperature was changed to 270° C. As a result, it was found that the conversion of methacrolein was 77.8% and the selectivity of methacrylic acid was 87.1%.

EXAMPLE 4

A catalyst having a composition, $P_{1.1}Mo_{12}V_{0.8}Cu_{0.2}K_{0.7}Cs_{0.2}Bi_{0.2}Sb_{0.7}(NH_4)_{0.4}$, was prepared according to Example 1 except that ammonium nitrate was used in place of ammonium carbonate, and 9.8 parts of ammonium nitrate per 100 parts of molybdenum trioxide was added. In this case, antimony pentoxide was used as a source of antimony. Using this catalyst, reaction was carried out under the same conditions as in Example 1 except that the reaction temperature was changed to 270° C. As a result, it was found that the conversion of methacrolein was 92.3% and the selectivity of methacrylic acid was 88.6%.

COMPARATIVE EXAMPLE 9

A catalyst was prepared in the same manner as in Example 4 except that, after refluxing cesium hydrogen carbonate and potassium carbonate were added with the temperature of the mixed solution kept at 100° C., and then ammonium nitrate was added with the temperature of the mixed solution kept at 100° C. Using this catalyst, reaction was carried out under the same conditions as in Example 1 except that the reaction temperature was changed to 270° C. As a result, it was found that the conversion of methacrolein was 90.8% and the selectivity of methacrylic acid was 88.6%.

COMPARATIVE EXAMPLE 10

A catalyst was prepared in the same manner as in Example 4 except not adding ammonium nitrate. Using this catalyst, reaction was carried out under the same conditions as in Example 1 except that the reaction temperature was changed to 290° C. As a result, it was found that the conversion of methacrolein was 87.4% and the selectivity of methacrylic acid was 87.5%.

Examples 5 to 7

Catalysts shown in Table 1 were prepared according to Example 1. In Table 1, part by weight of ammonium sulfate, ammonium hydrogen carbonate or ammonium carbonate means part by weight per 100 parts by weight of molybdenum trioxide. Solution temperature at addition means the solution temperature when materials for thallium, potassium and/or cesium components and ammonium sulfate, ammonium hydrogen carbonate or ammonium carbonate are added.

Using these catalysts, reaction was carried out in the same manner as in Example 1 except that the reaction temperature was changed. The results are collectively shown in Table 1.

EXAMPLES 8 to 10

Catalysts shown in Table 1 were prepared according to Example 3. In Table 1, part by weight of ammonium carbonate, ammonium sulfate and/or ammonium hydrogen sulfate means part by weight per 100 parts by weight of molybdenum trioxide. Solution temperature at addition means the solution temperature when materials for potassium, cesium or rubidium component and ammonium carbonate, ammonium sulfate and/or ammonium hydrogen sulfate area added.

Using these catalysts, reaction was carried out in the same manner as in Example 1 except that the reaction temperature was changed. The results are collectively shown in Table 1.

TABLE 1

| | Composition of catalyst | Amount of ammonium salt added (part) | Solution temperature at addition (°C.) | Reaction temperature (°C.) | Conversion of methacrolein (%) | Selectivity methacrylic acid (%) |
|---|---|---|---|---|---|---|
| Example 5 | $P_1Mo_{12}V_{0.5}Cu_{0.1}Tl_{0.8}Fe_{0.3}Zr_{0.1}Cr_{0.2}(NH_4)_{0.3}$ | Ammonium sulfate, 10 | 65 | 280 | 90.0 | 87.2 |
| Example 6 | $P_{1.1}Mo_{12}V_{0.5}Cu_{0.1}K_{0.8}Cs_{0.3}Fe_{0.3}Mg_{0.2}Te_{0.2}(NH_4)_{0.2}$ | Ammonium hydrogencarbonate, 8 | 45 | 280 | 90.5 | 87.3 |
| Example 7 | $P_{1.2}Mo_{12}V_{0.8}Cu_{0.1}K_1Fe_{0.3}Ge_{0.2}B_{0.3}(NH_4)_{0.2}$ | Ammonium carbonate, 8 | 60 | 275 | 91.1 | 87.7 |
| Example 8 | $P_{1.2}Mo_{12}V_{0.6}Cu_{0.2}K_1Bi_{0.3}Sb_{0.2}Ba_{0.2}(NH_4)_{0.3}$ | Ammonium carbonate, 7 | 55 | 280 | 90.1 | 89.0 |
| Example 9 | $P_1Mo_{12}V_{0.5}Cu_{0.2}Cs_1Fe_{0.3}Sb_{0.6}La_{0.1}Ag_{0.05}(NH_4)_{0.5}$ | Ammonium sulfate, 10 | 50 | 280 | 90.3 | 88.3 |
| Example 10 | $P_1MO_{12}V_{0.8}Cu_{0.1}Rb_1Zn_{0.2}Fe_{0.2}Sb_{0.7}W_{0.1}(NH_4)_{0.1}$ | Ammonium sulfate, 6 + ammonium hydrogensulfate, 3 | 70 | 280 | 91.3 | 88.9 |

What is claimed is:

1. A process for preparing a multicomponent catalyst, suitable for use in the production of methacrylic acid, represented by the general formula:

$$P_aMo_bV_cCu_dX_eY_f(NH_4)_gO_h$$

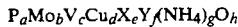

wherein P, MO, V, Cu, $NH_4$ and O are phosphorus, molybdenum, vanadium, copper, ammonium group and oxygen, respectively, X is at least one element selected from the group consisting of potassium rubidium, cesium and thallium, Y is at least one element selected from the group consisting of silver, magnesium, zinc, arsenic, germanium, silicon, tungsten, boron, bismuth, chromium, lanthanum, barium, antimony, iron, zirconium, tellerium and cerium, and a, b, c, d, e, f and H are an atomic ration of each element, and when b is 12, a is 0.5 to 3, c is 0.01 to 3, d is 0.01 to 2, e is b 0.1 to 2 and f is 0 to 5, and h is the number of oxygen atoms necessary to satisfy the valence of each component, and g is the number of ammonium groups being 0.01 to 2; which process comprises:

mixing oxides of molybdenum and vanadium, water, and compounds of phosphorus, copper and element y to form a mixed solution;

heating and reacting together said mixed solution at a temperature of at least 85° C. for about 1 to 10 hours;

cooling said reacted solution to a temperature of 80° C. or less;

adding, to said cooled solution, a source of at least one element designated as x while maintaining the temperature of said solution at 80° C. or less;

further adding to said cooled solution at least one ammonium compound selected from the group consisting of ammonium nitrate, ammonium carbonate, ammonium sulfate, ammonium hydrogen carbonate, and ammonium hydrogen sulfate, while maintaining the temperature of said solution at 80° C. or less;

removing water from said solution; and heat treating the residual product to produce a catalyst.

2. The process as claimed in claim 1 wherein said source of said element designated as x, and said ammonium compound are added sequentially.

3. The process as claimed in claim 1 wherein said cooled solution is maintained at a temperature of about 35 to 70° C. before and during the addition of said source of group x element.

4. The process as claimed in claim 2 wherein said ammonium compound is added to a solution maintained at about 40 to 70° C. after said group x source has been added thereto.

5. The process as claimed in claim 11 wherein said amount of said ammonium compound added is about 0.5 to 30 weight percent based on the total weight of all of the materials in said catalyst.

6. The product of the process of claim 1.

* * * * *